(12) United States Patent
Dettmar et al.

(10) Patent No.: US 6,306,789 B1
(45) Date of Patent: Oct. 23, 2001

(54) MUCOADHESIVE GRANULES OF CARBOMER SUITABLE FOR ORAL ADMINISTRATION OF DRUGS

(75) Inventors: Peter William Dettmar, Patrington; Paul Andrew Dickson, Hull; Frank Chadwick Hampson, Hedon; Ian Gordon Jollife, Cottingham; William Peers, Sproatley, all of (GB)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 0 days.

(21) Appl. No.: 09/416,400

(22) Filed: Oct. 12, 1999

Related U.S. Application Data

(62) Division of application No. 08/614,302, filed on Mar. 12, 1996, now abandoned.

(30) Foreign Application Priority Data

Mar. 13, 1995 (GB) .................................................. 9505032

(51) Int. Cl.[7] ........................................................ A61K 9/50
(52) U.S. Cl. ............................................ 501/490; 424/487
(58) Field of Search ..................................... 424/490, 501, 424/487; 514/819, 926–27, 772.6; 264/5–6

(56) References Cited

U.S. PATENT DOCUMENTS

| | | | |
|---|---|---|---|
| 4,675,339 | 6/1987 | Inoue et al. | 514/419 |
| 5,213,794 | 5/1993 | Fritsch et al. | 424/78.01 |
| 5,350,584 | * 9/1994 | McClelland et al. | |

FOREIGN PATENT DOCUMENTS

| | | |
|---|---|---|
| 0 183 424 A1 | 6/1986 | (EP) . |
| 0 284 039 A2 | 9/1988 | (EP) . |
| 0 297 866 A2 | 1/1989 | (EP) . |
| A 0 455 475 | 11/1991 | (EP) . |
| 0 514 008 A1 | 11/1992 | (EP) . |
| 0 533 297 A1 | 3/1993 | (EP) . |
| 0 642 797 A1 | 3/1995 | (EP) . |

* cited by examiner

Primary Examiner—Edward J. Webman
(74) Attorney, Agent, or Firm—Fish & Richardson P.C.

(57) ABSTRACT

Mucoadhesive granules comprising
a) carbomer and/or a salt thereof; and
b) an inert filler.

The granules preferably further comprise a pharmaceutically active agent suitable for sustained release into the gastrointestinal tract or for targeted delivery to the gastrointestinal mucosa.

8 Claims, No Drawings

MUCOADHESIVE GRANULES OF CARBOMER SUITABLE FOR ORAL ADMINISTRATION OF DRUGS

This application is a divisional application of U.S. Ser. No. 08/614,302, filed Mar. 12, 1996, now abandoned and claims the benefit of Great Britain Serial No. 9505032.4, filed Mar. 13, 1995.

The present invention relates to mucoadhesive granules of carbomer and in particular to such granules containing pharmaceutical active agents suitable for sustained release into the gastrointestinal tract or for targeted delivery to the gastrointestinal mucosa.

The problems associated with conventional oral administration of drugs are well known. For example following oral administration of a drug, peak blood level concentrations are attained which then decline until there is a repeat administration. To maintain the mean blood level concentrations at a therapeutic level either frequent dosing or less frequent dosing but at a higher level is generally required. The former can result in poor patient compliance while with the latter there may be an unacceptable level of side effects, which depend upon the drug being used.

Therefore various attempts have been made to produce sustained release dosage forms for orally administered drugs. There have been a number of different approaches. One of the most commonly used is the application of polymers to coat particles of drug substance. Commonly used coating polymers include those which are insoluble or slowly soluble but are permeable, so allowing gradual release of dissolved drug from the particles as they pass through the gastrointestinal tract. The disadvantages of this system include the possibility of sudden drug release when the coat is breached and dependence upon gastrointestinal transit time (which varies greatly between individuals)

A further method of improved drug delivery that has been suggested is to combine the active agent with a mucoadhesive agent. Various mucoadhesive agents are known which are believed to bind to the mucus layers coating the stomach and other regions of the gastrointestinal tract. It is believed that using such agents in combination with an active agent will result in the active agent also being bound to the mucus layer, leading either to slow release into the gastrointestinal tract or direct delivery to the gastrointestinal mucosa.

Carbomers and their salts are particularly useful agents for such drug delivery as they have good mucoadhesive activity. Furthermore carbomers are themselves known to produce beneficial effects in the gastrointestinal tract and on the gastrointestinal mucus.

One disadvantage of mucoadhesive powders is the possibility that they may form large aggregates on arrival in the stomach, leading to poor release of the active agents or to uneven application to the mucus layers. Thus granular forms of mucoadhesives are considered to be preferential. It would also be preferable if the active agent could be mixed as closely as possible with the granular mucoadhesive i.e, if they were mixed in the same granules. A simple method for preparing such granules requiring as few process steps as possible and as few expensive excipients (for example complex binding agents) would therefore be very valuable.

In a first aspect of the invention there are therefore provided mucoadhesive granules comprising
  a) carbomer and/or a salt thereof (hereinafter component a); and
  b) an inert filler (hereinafter component b).

Carbomers are synthetic high molecular weight polymers of acrylic acid cross linked with either alkyl esters of sucrose or pentaerythritol. Suitable commercially available grades of carbomer include Carbopol 910, Carbopol 934P, Carbopol 940, Carbopol 941, Carbopol 971P, Carbopol 974P, Carbopol 980, Carbopol 981, Carbopol 1342, Rheogic 252L and Rheogic 250H (both available from Nikon Junyaku)and Hostacerin PN73 (available from Hoechst UK).

Salts of carbomer may be complete salts (where all of the acid groups have been neutralised) or partial salts (in which only a proportion of the acid groups have been neutralised). Where salts of carbomer are referred to it will be understood that this includes complete salts, partial salts or mixtures thereof.

Preferred salts of carbomer are mono or divalent salts, most preferably sodium or potassium salts.

Suitable inert fillers include carbohydrates (for example dextrose, sucrose, mannitol, lactose, starch or microcrystalline cellulose) or inorganic salts (for example dicalcium phosphate, tricalcium phosphate or magnesium carbonate)

Preferably the inert filler is microcrystalline cellulose.

The mucoadhesive granules of the invention preferably comprise from 5 to 50% w/w carbomer and/or a salt thereof, more preferably 10 to 45% w/w and most preferably 15 to 40% w/w.

The mucoadhesive granules of the invention preferably comprise from 5 to 94% w/w inert filler, more preferably 15 to 75% w/w.

The mucoadhesive granules of the invention may also comprise an active agent suitable for sustained release into the gastrointestinal tract or for targeted delivery to the gastrointestinal mucosa.

There are therefore further provided mucoadhesive granules comprising
  a) carbomer and/or a salt thereof;
  b) an inert filler; and
  c) a pharmaceutically active agent (hereinafter component c) suitable for sustained release into the gastrointestinal tract or for targeted delivery to the gastrointestinal mucosa.

Pharmaceutically active agents suitable for sustained release into the gastrointestinal tract (component c1) are well known and include antimicrobial agents, analgesics, local anaesthetics, cardiovascular drugs, antacids, antiinflamatories, antitussives, H2-receptor antagonists and antidepressants. Preferably component c1) is either a compound having poor solubility in the gastrointestinal lumen, or it is combined with release retarding components to delay its release from the mucoadhesive granules of the invention.

Pharmaceutically active agents suitable for targeted delivery to the gastrointestinal mucosa (component c2) include antimicrobial agents (for example antibiotics or antiseptic agents), proton pump inhibitors (for example omeprazole), prokinetic/gastric emptying agents (e.g. cisapride), H2-receptor antagonists, local anaesthetics, antacids or ulcer healing agents. Preferably component c2) has poor solubility in the gastrointestinal lumen.

It is preferred that the solubility of component c2) is greater in neutral or basic conditions than in acid conditions. An example of a compound having the preferred properties of component c2) is triclosan.

It will be appreciated that many compounds may be equally suitable for use as component c1) or component c2).

Preferably component c) is an antimicrobial agent, more preferably triclosan or a derivative thereof.

The term "triclosan or a derivative thereof" as used herein is intended to encompass the use of an amount of an ester of triclosan or a derivative thereof, a cationic salt or an ester of triclosan or a derivative thereof which will provide the equivalent amount of triclosan or the said derivative thereof.

Examples of esters of triclosan or esters of the derivatives thereof for use in the present invention are the phosphate, phosphonate, sulfate, glucuronide, succinate and glutamate esters. Particularly preferred esters are the phosphate esters of triclosan.

The phosphate esters may be prepared by the phosphorylation of triclosan or a derivative thereof, using methods well known in the art.

The esters may be present in the form of the cationic salts thereof, for example the sodium, potassium, calcium or magnesium salts.

The cationic salts of triclosan may also be used in the present invention, for example, the sodium or potassium salts.

Derivatives of triclosan which may be used in the present invention further include those compounds in which one or both of the phenyl groups is/are substituted by one or more substituent groups in addition to the chloro substituents already present on the phenyl rings. Examples of suitable substituents are alkyl groups containing 1 to 4 carbon atoms, haloalkyl groups containing 1 to 4 carbon atoms, alkoxy groups containing 1 to 4 carbon atoms, cyano, allyl, amino and acetyl groups. Preferred substituents are methyl, methoxy and trifluoromethyl groups. It will be understood that if triclosan is substituted by more than one substituent, then the substituents may be the same or different.

Most preferably component c) is triclosan.

When present in the mucoadhesive granules of the invention component c) preferably comprises 0.01 to 70% by weight of the total granular weight, more preferably 0.1 to 50% and most preferably 1 to 35.

The mucoadhesive granules of the invention may optionally further comprise one or more disintegrants, for example sodium starch glycolate, croscarmellose sodium or crospovidone. Where used the disintegrants preferably comprise no more than 30% w/w of the mucoadhesive granules of the invention.

Where component c) is triclosan or a derivative thereof it is preferred that the mucoadhesive granules of the invention further comprise a solvent and/or an aqueous solubility enhancing agent for the triclosan or derivative thereof.

There are therefore yet further provided mucoadhesive granules comprising:
a) carbomer and/or a salt thereof;
b) an inert filler;
c) triclosan or a derivative thereof; and
d) a solvent and/or an aqueous solubility enhancing agent for the triclosan (hereinafter component d).

Component d) is selected from those agents in which triclosan or its derivatives are soluble and/or those agents which improve the aqueous solubility of triclosan or its derivatives.

Component d) is preferably selected from alcohols, polyalcohols, surfactants or mixtures thereof. More Component d) is preferably selected from solvents, such as alcohols or polyalcohols, or solubility enhancing agents, such as surfactant, or mixtures thereof. More preferably component d) is selected from polyethylene glycols, propylene glycol, anionic surfactants or mixtures thereof. Most preferably component c) is propylene glycol, sodium lauryl sulphate or mixtures thereof.

Where component d) is an alcohol or a polyalcohol it preferably comprises from 1 to 20% by weight of the total weight of the mucoadhesive granules of the invention, more preferably from 2 to 15%.

Where compound d) is a surfactant it preferably comprises from 0.1 to 5% by weight of the mucoadhesive granules of the invention, more preferably from 0.2 to 3%.

The mucoadhesive granules of the invention in which component c) is triclosan or a derivative thereof are particularly suitable for the preparation of a medicament for the treatment of gastrointestinal disorders associated with *Helicobacter pylori* infections.

The mucoadhesive granules of the invention are particularly easy and economical to manufacture because the carbomer and/or carbomer salts will act as a binding agent so removing or reducing the need for extra excipients.

Therefore it is preferred that no binding agents (other than carbomers and/or salt thereof) are used in the granulation stage of the preparation of the mucoadhesive granules of the invention. Most particularly it is preferred that no water insoluble anionic polymers are used as binding agents in the granulation stage of the manufacture of the mucoadhesive granules of the invention.

The mucoadhesive granules of the invention may therefore simply be manufactured by blending components a) and b), and granulating with a granulation fluid. The granules so formed may be used in the wet state or they may be dried by any conventional means.

If component c) is to be incorporated into the mucoadhesive granules of the invention it may be added either with components a) and b) or dissolved in the granulation fluid.

There is therefore provided a process for the preparation of the mucoadhesive granules of the invention by
i) mixing a carbomer and/or a salt thereof (component a) with component b) plus, optionally, component c);
ii) applying to the mixture i) a granulating fluid (optionally comprising component c) whilst blending; and, optionally,
iii) drying the prepared granules.

The granulation fluid may be any suitable fluid which is compatible with the components of the granules. The granulation fluid should be one which is relatively easily removable from the granules during drying, or which is safe for human consumption if the granules are not to be dried. Preferably the granulation fluid is an alcohol (e.g. ethanol or isopropanol), a polyalcohol (e.g. glycerol or polyethylene glycol 300), water or a mixture thereof. Most preferably the granulation fluid is water.

The amount of granulation fluid necessary will depend upon the nature of the components used, the nature of the granulation fluid and the scale of manufacture. The amount necessary may be determined by simple observation of the wet granules.

Granulation times plus drying times and temperatures will also depend upon the nature of the components, and the scale of manufacture. They may be determined by simple experimentation.

A further advantage of the invention is that where component a) is a salt of a carbomer, or a mixture of a carbomer and a salt thereof the salts may be prepared in situ as part of the process. This may be achieved by use of a base or a basic salt which will react with the carbomer to form a salt thereof. The base or basic salt may be added either in step i) or step ii).

There is therefore provided a process for the preparation of the mucoadhesive granules of the invention wherein component a) is a carbomer salt, or a mixture of carbomer and a salt thereof, by
i) mixing a carbomer with component b) plus, optionally, component c);
ii) applying to the mixture i) a granulating fluid (optionally comprising component c) whilst blending; and, optionally, iii) drying the prepared granules;
   wherein a base or a basic salt is added either in step i) or step ii).

There is further provided a process for the preparation of the mucoadhesive granules of the invention wherein component a) is a carbomer salt, or a mixture of carbomer and a salt thereof, by
   i) mixing a carbomer with component b) plus a base or a basic salt plus, optionally, component c);
   ii) applying to the mixture i) a granulation fluid (optionally comprising component c) whilst blending; and, optionally,
   iii) drying the prepared granules.

There is yet further provided a process for the preparation of the mucoadhesive granules of the invention wherein component a) is a carbomer salt or a mixture of carbomer and a salt thereof, by
   i) mixing a carbomer with component b) plus, optionally, component c);
   ii) applying to the mixture i) a granulation fluid further comprising a base or a basic salt and, optionally, component c) whilst blending; and, optionally,
   iii) drying the prepared granules.

Preferred bases for use in the invention include sodium hydroxide and potassium hydroxide. Preferred basic salts include sodium bicarbonate, sodium carbonate, calcium carbonate, potassium carbonate and potassium bicarbonate.

Where component c) is included in step 1) of the preparation of the mucoadhesive granules of the invention it may be included either
   i) by dry mixing with components a) and b), or
   ii) where component c) is not readily soluble in the granulation fluid, by dissolving component c) in a suitable solvent, mixing the solvent with components a) and b); and optionally removing the solvent by pre drying before application of the granulation fluid, or during the drying of the granules.

If component d) is to be incorporated into the mucoadhesive granules of the invention, it may be added either with component a) and b) or mixed with the granulation fluid.

Any other optional ingredients in the mucoadhesive granules of the invention may be added either with components a) and b) or mixed with the granulation fluid depending upon their compatabilities and form etc. The method of addition will be based on conventional granulation procedures.

Further according to the invention there is provided a pharmaceutical composition (hereinafter the pharmaceutical composition) comprising mucoadhesive granules of the invention.

The pharmaceutical compositions of the invention are suitable for providing sustained release of active agents (or carbomer and/or salts of carbomer) into the gastrointestinal tract, or for the targeted delivery of active agents (or carbomer and/or salts of carbomer) to the gastrointestinal mucosa.

The pharmaceutical compositions of the invention may preferably be in the form of granules or tablets, including chewable tablets. When the compositions are in the form of granules they may be supplied to a patient in sachets or filled into capsules.

The pharmaceutical compositions of the invention may further comprise suitable known excipients including fillers, disintegrants or effervescent systems, lubricants, glidants, flavours and colouring agents.

The pharmaceutical compositions of the invention may also comprise further pharmaceutically active agents. The further pharmaceutically active agents may be the same as component c) but not in a mucoadhesive form, or may be suitable complementary pharmaceutically active agents.

Mucoadhesive granules of the invention preferably make up 5 to 100% by weight of the pharmaceutical compositions of the invention, more preferably 25 to 100%, most preferably 50 to 99%.

Where the pharmaceutical compositions of the invention comprise granules filled into gelatine capsules the capsules are preferably hard gelatine capsules.

Mucoadhesive granules of the invention may be filled into capsules by using conventional capsule filling machinery.

Where the pharmaceutical compositions of the invention are tablets (other than chewable tablets) they preferably also comprise at least one disintegrant.

The disintegrants may be contained in the mucoadhesive granules of the invention (intragranular) or may be separately mixed with the granules (extragranular). Intragranular and extragranular disintegrants may be included in the same compositions. Where the pharmaceutical compositions of the invention contain both intragranular and extragranular disintegrants these may be the same or different.

The extragranular disintegrants are preferably rapidly acting disintegrants, for example sodium starch glycolate, croscarmellose sodium, croscarmellose calcium or crospovidone.

Where the pharmaceutical compositions of the invention are in the form of tablets comprising extragranular disintegrants they will preferably comprise from 0.5 to 20% w/w extragranular disintegrant, more preferably 1 to 10% w/w, most preferably 1 to 5% w/w.

Where the pharmaceutical compositions of the invention are in the form of tablets they may be produced by any conventional tableting process.

In a preferred embodiment there is provided a pharmaceutical composition in the form of a tablet comprising
   a) 50 to 99% w/w of the mucoadhesive granules of the invention, and
   b) 1 to 5% w/w of an extragranular, rapidly acting tablet disintegrant.

There is further provided the use of such a preferred embodiment for the sustained release of a pharmaceutically active agent (or carbomer and/or a salt of carbomer) into the gastrointestinal tract, or for targeted delivery of a pharmaceutically active agent (or carbomer and/or a salt of carbomer) to the gastrointestinal mucosa.

The invention will now be illustrated by reference to the following examples:

EXAMPLE 1

Granules of carbomer and sodium carbomer were prepared according to the following process.

|  | g/batch |
| --- | --- |
| Carbopol 934 P | 1000 |
| Microcrystalline cellulose | 2730 |
| Sodium bicarbonate* | 200 |
| Granulation fluid - water |  |

*a proportion of the sodium bicarbonate was lost as water and carbon dioxide during the granulation The Carbopol, microcrystalline cellulose and sodium bicarbonate were blended in a high speed mixer/granulator.

Approximately 1.5L of water was sprayed onto the powders whilst mixing until granulation was complete.

The wet mass was dried in a fluid bed drier at 600° C. until the residual water content was less than 5 w/w. The resulting granules were screened through a 20 mesh screen.

EXAMPLE 2

Mucoadhesive granules containing carbomer, sodium carbomer and triclosan are prepared according to the following process.

|  | g/batch |
|---|---|
| Triclosan | 20 |
| Carbopol 974 P | 100 |
| Microcrystalline cellulose | 300 |
| Sodium bicarbonate* | 20 |
| Granulation fluid - water | |

*a proportion of the sodium bicarbonate is lost as water and carbon dioxide during the granulation.

The Carbopol and microcrystalline cellulose are blended in a high speed food processor.

The triclosan is dissolved in 50 ml of isopropyl alcohol and the solution added to the dry mixture whilst blending.

The isopropyl alcohol is removed by forced air drying at 20° C. (to a residual solvent concentration of less than 0.5% w/w).

The powder is screened through a 20 mesh screen and the sodium bicarbonate is blended in.

Approximately 50 ml of water is sprayed onto the powder whilst mixing until granulation is complete.

The wet mass is dried in a fluid bed drier at 400° C. until the residual water content is less than 5% w/w.

The granules are screened to a maximum particle size of 500 μm.

EXAMPLE 3

Capsules containing mucoadhesive granules of carbomer, sodium carbomer and triclosan are prepared by the following process.

The granules of Example 2 are blended with 10 g of crosspovidone and 2.5 g of magnesium stearate, and filled into size 0 hard gelatine capsules to give a fill weight of 219 mg per capsule.

EXAMPLE 4

Mucoadhesive granules containing carbomer, sodium carbomer and triclosan were prepared according to the following process.

|  | g/batch |
|---|---|
| Triclosan | 12.50 |
| Carbopol 974 P | 83.33 |
| Calcium carbonate | 83.33 |
| Disodium edetate | 63.75 |
| Microcrystalline cellulose | 225.42 |
| Sodium bicarbonate* | 16.67 |
| Granulation fluid - water | |

*A proportion of the sodium bicarbonate was lost as water and carbon dioxide during the granulation.

The Carbopol, calcium carbonate, disodium edetate and microcrystalline cellulose were mixed in a high speed food processor.

The triclosan was dissolved in 30 ml of isopropyl alcohol and the solution was added to the dry powders and mixed.

The residual solvent was removed by forced air drying at 20° C. until the concentration in the powder was below 0.5% w/w.

The sodium bicarbonate was added to the dried mixture and blended well.

The mixture was granulated with approximately 55 ml of water.

The wet mass was dried by fluid bed drying at 40° C. until the residual water content was below 5% w/w.

The dried granules were screened through a 20 mesh screen.

EXAMPLE 5

Tablets containing mucoadhesive granules comprising carbomer, sodium carbomer and triclosan were prepared by the following process.

The granules of Example 4 were blended with 25 g of sodium starch glycolate and 2.5 g magnesium stearate. The mixture was compressed in a tablet press to give tablets of 600 mg fill weight.

EXAMPLE 6

Mucoadhesive granules containing carbomer, sodium carbomer and triclosan are prepared by the following process.

|  | g/batch |
|---|---|
| Triclosan | 15 |
| Carbopol 934 P | 100 |
| Microcrystalline cellulose | 342 |
| Sodium hydroxide | 10 |

The carbomer and microcrystalline cellulose are dry mixed in a high speed food processor.

The sodium hydroxide is dissolved in 50 ml of water in a separate vessel. The triclosan is added and mixed well.

Granules are formed by slowly adding the caustic solution onto the powder mix, whilst blending.

The wet mass is dried in a fluid bed dryer at 40° C. until the residual water content is less than 5%.

The granules are screened through a 20 mesh screen.

EXAMPLE 7

Tablets containing mucoadhesive granules comprising carbomer, sodium carbomer and triclosan are prepared according to the following process.

The granules of Example 6 are blended with 30 g croscarmellose sodium and 3 g magnesium stearate.

The mixture is compressed in a tablet press to give tablets having a fill weight of 500 mg.

EXAMPLE 8

Mucoadhesive granules comprising carbomer, potassium carbomer and amoxycillin are prepared according to the following process.

| | g/batch |
|---|---|
| Amoxycillin trihydrate | 125 |
| Carbopol 934P | 125 |
| Lactose | 185.8 |
| Potassium bicarbonate * | 30 |
| Granulation fluid - water | |

* A proportion of the potassium bicarbonate is lost as water and carbon dioxide during the granulation.

The amoxycillin, carbomer, lactose and potassium bicarbonate are mixed in a high speed food processor.

Approximately 50 ml of water is added to the powder whilst mixing at high speed to form granules.

The granules are dried at 20° C. in a fluid bed dryer, to a residual water content of less than 5%, and screened to a granule size of 850 µm.

The granules may be formed into tablets by blending with 50 g calcium carbonate and 2.5 g of magnesium stearate and pressing on a tablet press to give tablets with a weight of 500 mg.

EXAMPLE 9

Mucoadhesive granules comprising carbomer, sodium carbomer and calcium carbonate are prepared according to the following process.

| | g/batch |
|---|---|
| Carbopol 934P | 50 |
| Calcium carbonate | 50 |
| Sodium bicarbonate* | 60 |
| Mannitol | 258 |
| Xylitol | 75 |
| Granulation fluid - water | |

*A proportion of the sodium bicarbonate is lost as water and carbon dioxide during the granulation.

All of the dry ingredients are blended in a high speed food mixer.

Approximately 60 ml of water is sprayed onto the powder whilst blending until granulation is complete.

The granules are dried in a fluid bed dryer at 60° C. to a residual water content of less than 5%.

The dried granules are sieved through a 500 µm screen.

The granules may be formed into tablets by blending with 12.5 g orange flavour, 1 g aspartame and 1 g magnesium stearate and pressing the mixture to give 1 g chewable tablets.

EXAMPLE 10

Mucoadhesive granules comprising carbomer, sodium carbomer and famotidine are prepared according to the following process.

| | g/batch |
|---|---|
| Famotidine | 4 |
| Carbopol 974 P | 20 |
| Microcrystalline cellulose | 88.4 |
| Sodium bicarbonate* | 4 |
| Granulation fluid - water | |

*A proportion of the sodium bicarbonate is lost as water and carbon dioxide during the granulation.

The dry ingredients are blended at high speed in a food mixer.

Approximately 10 ml of water is sprayed onto the powder whilst blending until granulation is complete.

The granules are dried at 40° C. in a fluid bed dryer until the residual water content is less than 5%.

The dried granules are screened to a size of 850 µm.

The granules may be formed into tablets by blending with 6 g sodium starch glycolate and 0.6 g magnesium stearate and compressing to give 600 mg tablets.

EXAMPLE 11

Tablets comprising mucoadhesive granules of carbomer were prepared according to the following process.

| | g/batch |
|---|---|
| Carbopol 974P | 1333 |
| Microcrystalline cellulose | 1980 |
| Granulation fluid - water | |

The Carbopol and microcrystalline cellulose were blended in a high shear mixer granulator.

Approximately 350 ml of water was sprayed onto the powders until granulation was complete.

The granules were dried in a fluid bed drier at 60° C. for 45 minutes.

The granules were milled to a size of less than 500 um.

The granules were blended with 666 g calcium carbonate and 20 g magnesium stearate and then pressed into 600 mg tablets.

EXAMPLE 12

Mucoadhesive granules comprising carbomer and triclosan were prepared according to the following process.

| | g/batch |
|---|---|
| Triclosan | 1428.6 |
| Carbopol 934P | 1428.6 |
| Microcrystalline cellulose | 785.7 |
| Propylene glycol | 357.1 |
| Granulating fluid - water | |

The triclosan, Carbopol and microcrystalline cellulose were blended in a high shear mixer granulator. The propylene glycol was added and blended in.

Approximately 400 ml of water was sprayed onto the mixture until granulation was complete.

The wet granules were screened through a 1 mm sieve and dried in a fluid bed drier at 40° C. for 60 minutes.

The dried granules were milled to a size of less than 500 um.

EXAMPLE 13

Tablets containing mucoadhesive granules comprising carbomer and triclosan were prepared according to the following process. 2840 g of the granules of Example 12 were blended with 1014.3 g calcium carbonate, 277.9 g microcrystalline cellulose, 63.9 g sodium starch glycolate, 42.6 g silicon dioxide and 21.3 g magnesium stearate.

The resulting mixture was compressed into 420 mg tablets.

EXAMPLE 14

The mucoadhesive and drug delivery properties of the granules of the invention were demonstrated by the following process.

A stomach of a freshly slaughtered pig was opened at the fundus region, the contents washed out and the opening sutured.

The stomach was equilibrated with 50 ml of simulated gastric medium at 37° C.

A tablet as prepared in Example 5 was introduced through the oesophagus and left to disperse for 30 minutes.

The stomach was then emptied through the pylorus, and a water wash introduced through the oesophagus and removed, also through the pylorus.

Examination of the stomach walls after cutting open revealed granules of the tablet dispersed widely over the stomach mucus. The mucus layer was also found to be considerably more viscous than that from a stomach tested with a tablet prepared as in Example 5 but omitting any carbomer.

Analysis of the mucus scraped off the stomach wall showed that more than 50 of the triclosan from the tablet as prepared in Example 5 was present in the mucus with the remainder being found in the simulated gastric medium and the water wash.

What is claimed is:

1. A process for the preparation of mucoadhesive granules which comprises the steps of: (i) mixing a carbomer and/or a salt thereof with an inert filler to obtain a mixture; (ii) adding to the mixture, whilst blending, a granulating fluid to obtain granules; and (iii) drying said granules.

2. A process for the preparation of mucoadhesive granules which comprises the steps of: (i) mixing a carbomer and/or a salt thereof with an inert filler and optionally with a pharmaceutically active agent to obtain a mixture; (ii) adding to the mixture, whilst blending, a granulating fluid, which optionally contains the pharmaceutically active agent, to obtain granules; and (iii) drying said granules.

3. A process for the preparation of mucoadhesive granules, said process comprising the steps of: (i) mixing a carbomer salt or a combination of carbomer and a salt thereof with an inert filler to obtain a mixture; (ii) adding to the mixture a granulating fluid to obtain granules; and (iii) drying said granules, wherein a base or a basic salt is included either in step (i) or in step (ii).

4. A process for the preparation of mucoadhesive granules, said process comprising the steps of: (i) mixing a carbomer salt or a combination of a carbomer and a salt thereof with an inert filler and optionally with a pharmaceutically active agent to obtain a mixture; (ii) adding to the mixture a granulating fluid which optionally contains the pharmaceutically active agent, to obtain granules; and (iii) drying said granules; wherein a base or a basic salt is included either in step (i) or in step (ii).

5. A process for tile preparation of mucoadhesive granules which comprises tie steps of (i) mixing a carbomer and/or a salt thereof with an inert filler to obtain a mixture; (ii) adding to the mixture, whilst blending, a granulating fluid to obtain granules, without passing the fluid-containing mixture through a, screen; and (iii) optionally drying said granules.

6. A process for the preparation of mucoadhesive granules which comprises the steps of: (i) mixing a carbomer and/or a salt thereof with an inert filler and optionally with a pharmaceutically active agent to obtain a mixture; (ii) adding to the mixture, whilst blending, a granulating fluid, which optionally contains the pharmaceutically active agent, to obtain granules, without passing the fluid-containing mixture through a screen; and (iii) optionally drying said granules.

7. A process for the preparation of mucoadhesive granules, said process comprising the steps of: (i) mixing a carbomer salt or a combination of carbomer and a salt thereof with an inert filler to obtain a mixture; (ii) adding to the mixture a granulating fluid to obtain granules, without passing the fluid-containing mixture through a screen; and (iii) optionally drying said granules, wherein a base or a basic salt is included either in step (i) or in step (ii).

8. A process for the preparation of mucoadhesive granules said process comprising the steps of: (i) mixing a carbomer salt or a combination of a carbomer and a salt thereof with an inert filler and optionally with a pharmaceutically active agent to obtain a mixture; (ii) adding to the mixture a granulating fluid which optionally contains the pharmaceutically active agent, to obtain granules, without passing the fluid-containing mixture through a screen; and (iii) optionally drying said granules; wherein a base or a basic salt is included either in step (i) or in step (ii).

* * * * *

UNITED STATES PATENT AND TRADEMARK OFFICE
CERTIFICATE OF CORRECTION

PATENT NO. : 6,306,789 B1
DATED : October 23, 2001
INVENTOR(S) : Peter William Dettmar et al.

It is certified that error appears in the above-identified patent and that said Letters Patent is hereby corrected as shown below:

<u>Column 12,</u>
Line 17, change "tile" to -- the --.
Line 18, change "tie" to -- the --.
Line 22, change "a," to -- a --.

Signed and Sealed this

Seventh Day of May, 2002

Attest:

JAMES E. ROGAN
*Attesting Officer*     *Director of the United States Patent and Trademark Office*